United States Patent [19]

Muetterties et al.

[11] 4,256,104

[45] Mar. 17, 1981

[54] EQUIPMENT SETS AND SYSTEM FOR THE SEQUENTIAL ADMINISTRATION OF MEDICAL LIQUIDS AT DUAL FLOW RATES

[75] Inventors: Andrew J. Muetterties, Gages Lake; Joseph N. Genese, Waukegan, both of Ill.

[73] Assignee: Abbott Laboratories, North Chicago, Ill.

[21] Appl. No.: 16,461

[22] Filed: Feb. 28, 1979

[51] Int. Cl.³ .............................................. A61M 5/14
[52] U.S. Cl. .................................. 128/214 G; 137/113; 137/177; 222/145
[58] Field of Search ............ 128/214 R, 214 C, 214 G, 128/214.2, 227; 222/129.2, 145; 137/113, 177, 183

[56] References Cited

U.S. PATENT DOCUMENTS

| 2,999,499 | 9/1961 | Willet | 128/214 G |
| 3,217,711 | 11/1965 | Pecina et al. | 128/214 C |
| 3,886,937 | 6/1975 | Bobo et al. | 128/214 G |
| 3,951,145 | 4/1976 | Smith | 128/214 C X |
| 3,965,895 | 6/1976 | Dabney | 128/214 C |
| 3,982,534 | 9/1976 | Buckman | 128/214 C |
| 4,005,710 | 2/1977 | Zeddies et al. | 128/214 R |
| 4,034,754 | 7/1977 | Virag | 128/214 G |
| 4,116,646 | 9/1978 | Edwards | 128/214 R X |

OTHER PUBLICATIONS

"Sets for Dual Containers", Abbott Labs. Catalogue, p. 12.

Primary Examiner—Dalton L. Truluck
Attorney, Agent, or Firm—Robert S. Beiser; Robert L. Niblack

[57] ABSTRACT

Gravitational flow system and equipment sets for the sequential administration of medical liquids wherein a primary liquid can be administered at a flow rate independent of the flow rate of a secondary liquid, and including a barrier substantially impervious to air to prevent the inadvertent administration of air when the secondary liquid is depleted.

24 Claims, 6 Drawing Figures

EQUIPMENT SETS AND SYSTEM FOR THE SEQUENTIAL ADMINISTRATION OF MEDICAL LIQUIDS AT DUAL FLOW RATES

BACKGROUND OF THE INVENTION

The present invention relates to systems and equipment sets for the administration of medical liquids to a patient, and more particularly, to systems and equipment sets for the sequential administration of a plurality of medical liquids.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250-2,000 ml. of the liquid. Such prolonged infusions commonly are administered at a flow rate of 10-150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liqiud resumed. Generally, the secondary liquid will be administered at a flow rate of 50-250 ml./hr.

Abbott Laboratories, North Chicago, Ill. manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary object of the present invention, therefore, is to provide a system for the sequential administration of medical liquids at dual flow rates that will not draw air from the secondary container when the secondary liquid has been depleted. Another object is to provide equipment sets that embody the system of this invention.

In accordance with these and other objects, there is provided by the present invention a gravitational flow system for the sequential administration of medical liquids to a patient including a primary liquid container, a primary tube, a secondary liquid container, a secondary tube, and a common tube all connected in fluid communication to form a primary liquid flow path and a secondary liquid flow path. The primary liquid flow path includes the primary and common tube, while the secondary liquid flow path includes the secondary and common tubes.

The primary tube includes a primary valve which allows primary liquid to flow from the primary container whenever the height of primary liquid is greater than or equal to the height of the secondary liquid in the system. The primary valve, which can be a backcheck valve, prevents primary liquid from flowing out of the primary container whenever the height of the primary liquid is less than the height of the secondary liquid in the system.

To establish the dual flow rates of the primary and secondary liquids, a secondary flow control means in the secondary liquid flow path for adjusting the flow rate of the secondary liquid and a primary flow control means on the primary tube for adjusting the flow rate of the primary liquid to a rate greater than, less than, or equal to the flow rate of the secondary liquid are provided. An air barrier in the secondary liquid flow path that is substantially impervious to air is provided to insure that no air is drawn from the secondary container when the secondary liquid is depleted.

BRIEF DESCRIPTION OF THE DRAWING

Other objects and attendant advantages will become ovvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
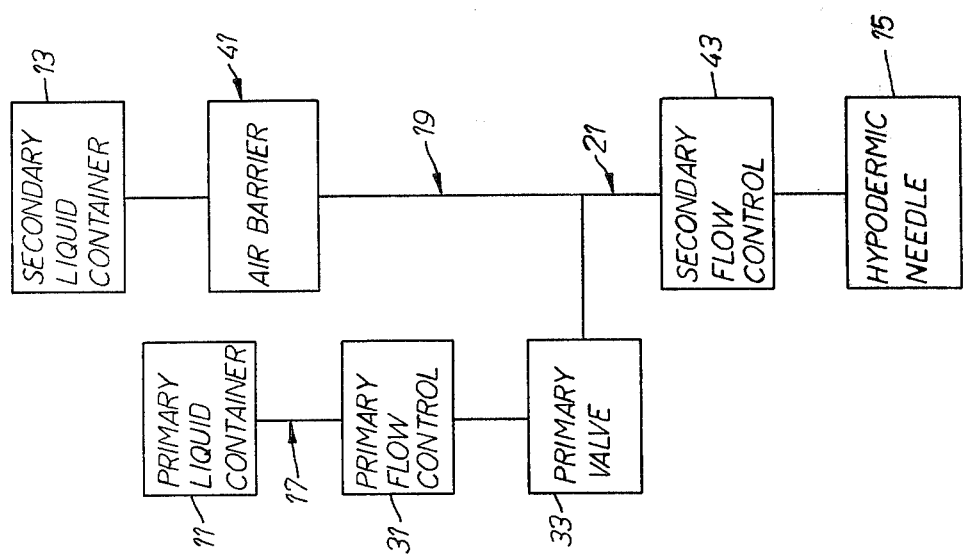
FIG. 1 is a schematic block diagram of the efficacious system for the sequential administration of medical liquids at dual flow rates contemplated by this invention.

Referring to the drawing, there is shown in FIG. 1, a schematic block diagram of the basic elements of the gravitational flow system for the sequential administration of medical liquids at dual flow rates contemplated by this invention.

Figure 2:
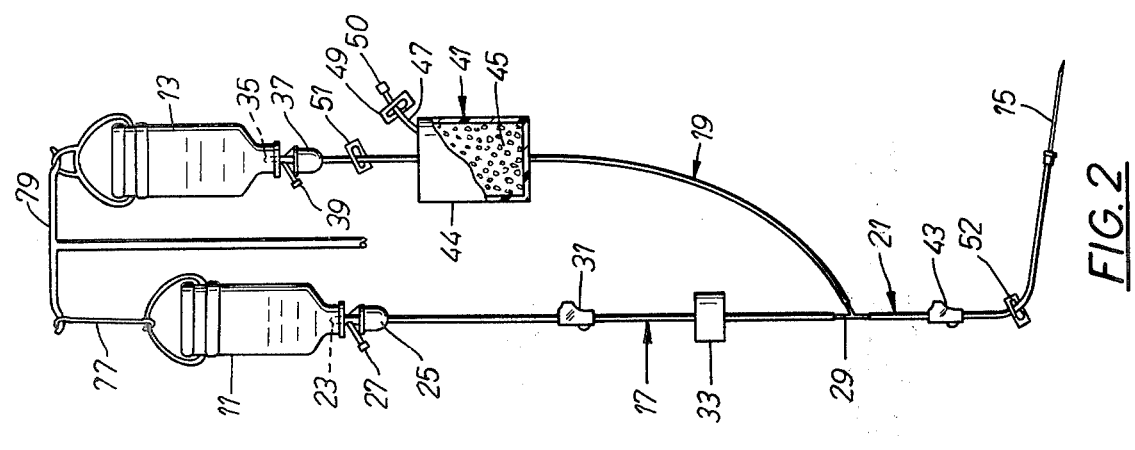
Figure 5:
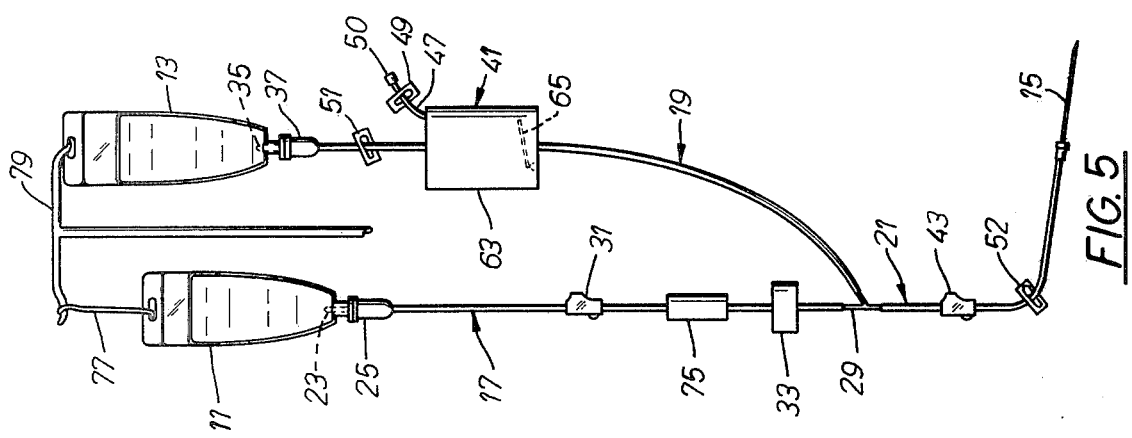

The diagram depicts a primary liquid container 11 that contains a primary medical liquid to be administered to a patient for a prolonged period of time. The diagram also depicts a secondary liquid container 13 that contains a secondary medical liquid to be administered to the patient for a relatively short period of time, during which time the administration of the primary liquid will be temporarily interrupted. As shown in the sets of FIGS. 2 and 5, containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

The distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 2, an integral, filtered air vent 27. Such piercing pins, drip chambers and air vents are well known in the medical practice and need not be more fully explained here.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively. Primary tube 17 has a primary flow control 31 intermediate its ends for independently adjusting the rate of flow of the primary liquid through the primary liquid flow path. Preferably, as shown in FIGS. 2-5, primary flow control 31 can be a roller clamp. However, it can be any other adjustable device that will reliably maintain a desired primary liquid flow rate.

Primary tube 17 includes a primary valve 33 between its proximal end and primary flow control 31. Primary valve 33 allows primary liquid to flow from primary container 11 whenever the height of the primary liquid is greater than or equal to the height of the secondary liquid in the system of FIG. 1. Further, primary valve 33 prevents the flow of primary liquid from primary container 11 whenever the height of the primary liquid is less than the height of the secondary liquid in the system.

While primary valve 33 has been shown in the sets of FIGS. 1-5 as being spaced from the proximal end of primary tube 17, it will be readily apparent that primary valve 33 can be incorporated into the primary leg of y-tube 29, if so desired. For example, primary valve 33 can be a conventional, one-way, backcheck valve mounted within the primary leg of y-tube 29.

The distal end of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 2, an integral, filtered air vent 39. The proximal end of secondary tube 19 is joined in fluid communication to the distal end of common tube 21, preferably, by a y-tube 29.

An air barrier 41 and secondary flow control 43 are located in the secondary liquid flow path. Preferably, as shown in FIGS. 2-5, secondary flow control 43 can be a roller clamp. However, it can be any other adjustable device that can reliably maintain a desired secondary liquid flow rate.

As shown in FIGS. 1-5, air barrier 41 is located in secondary tube 19, which is its preferred location. However, air barrier 41 can be located in common tube 21, if so desired. Likewise, for increased reliability of the system, a plurality of air barriers 41 can be located in either the secondary tube 19, common tube 21, or both. Further, while air barrier 41 is shown spaced from the proximal end of secondary tube 19, it will be readily apparent that air barrier 41 can be incorporated into the secondary or common tube leg of y-tube 29.

As shown in the set of FIG. 2, air barrier 41 comprises a housing 44 having an inlet and outlet in fluid communication with secondary tube 19 and constitutes a portion of it. Housing 44 is filled with a hydrophilic membrane filter 45 which is impermeable to air when wet. The hydrophilic filters can be formed from materials such as a cellulose acetate material produced by the Millipore Filter Corporation of Bedford, Mass. or the Sartorius-Membranfilter GmbH of Weender Landstr, West Germany.

The housing of each set shown in FIGS. 2-5 also includes an air vent tube 47 having a slide clamp 49 and a filtered opening 50. Alternatively, opening 50 can be filtered by a hydrophobic membrane filter which is permeable by air, but not liquids. The hydrophobic filters can be formed of polyfluorotetraethylene, hexafluoropropylene/tetrafluoroethylene copolymer, or other suitable materials. One such filter is made of Gelman ANH-450 material made by Gelman Instruments of Ann Arbor Mich. When such a hydrophobic filter is used, slide clamp 49 can be eliminated.

Each embodiment of the system of FIG. 1 shown in FIGS. 2-5 includes a slide clamp 51 near the distal end of secondary tube 19 and a slide clamp 52 near the proximal end of common tube 21.

Figure 3:
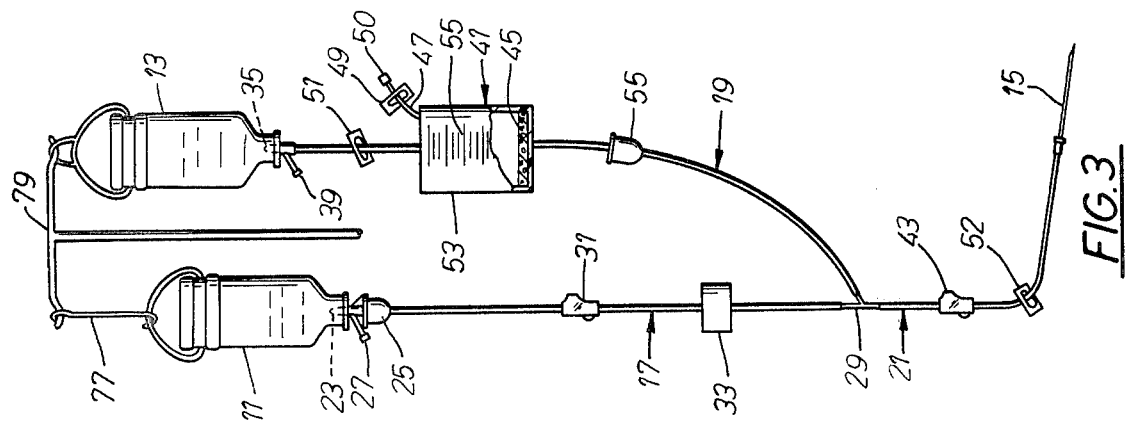
FIGS. 2-5 are front elevational views of four medical liquid administration equipment sets embodying the system of FIG. 1.

The air barrier 41 shown in the set of FIG. 3 comprises a housing 53 that is substantially transparent and has graduations 55 on its sidewall that indicate the amount of liquid contained therein. Housing 53 has an inlet and outlet in fluid communication with secondary tube 19 and constitutes a portion of it. The outlet from housing 53 is covered by a hydrophilic membrane filter 45. In the set of FIG. 3, secondary tube 19 includes a drip chamber 55 on the proximal side of air barrier 41.

Figure 4:
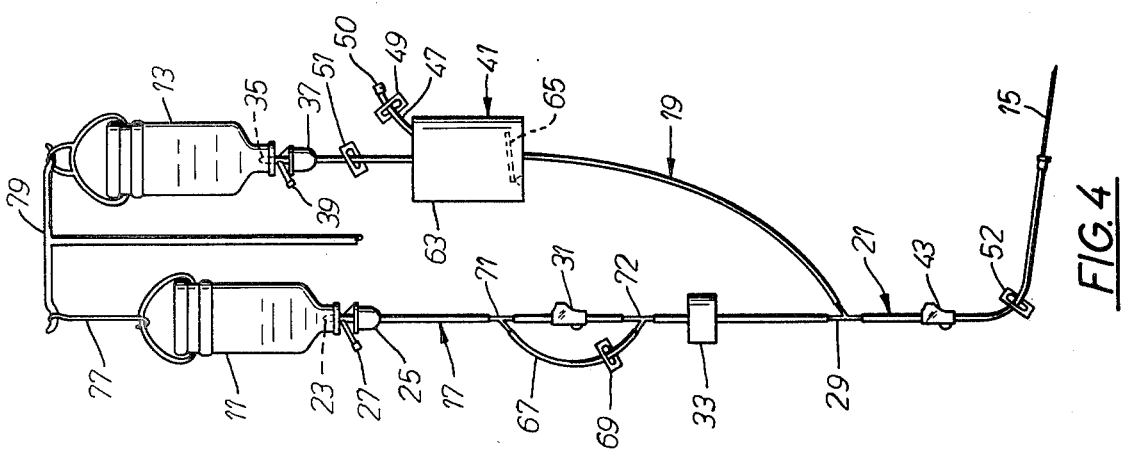
Figure 6:
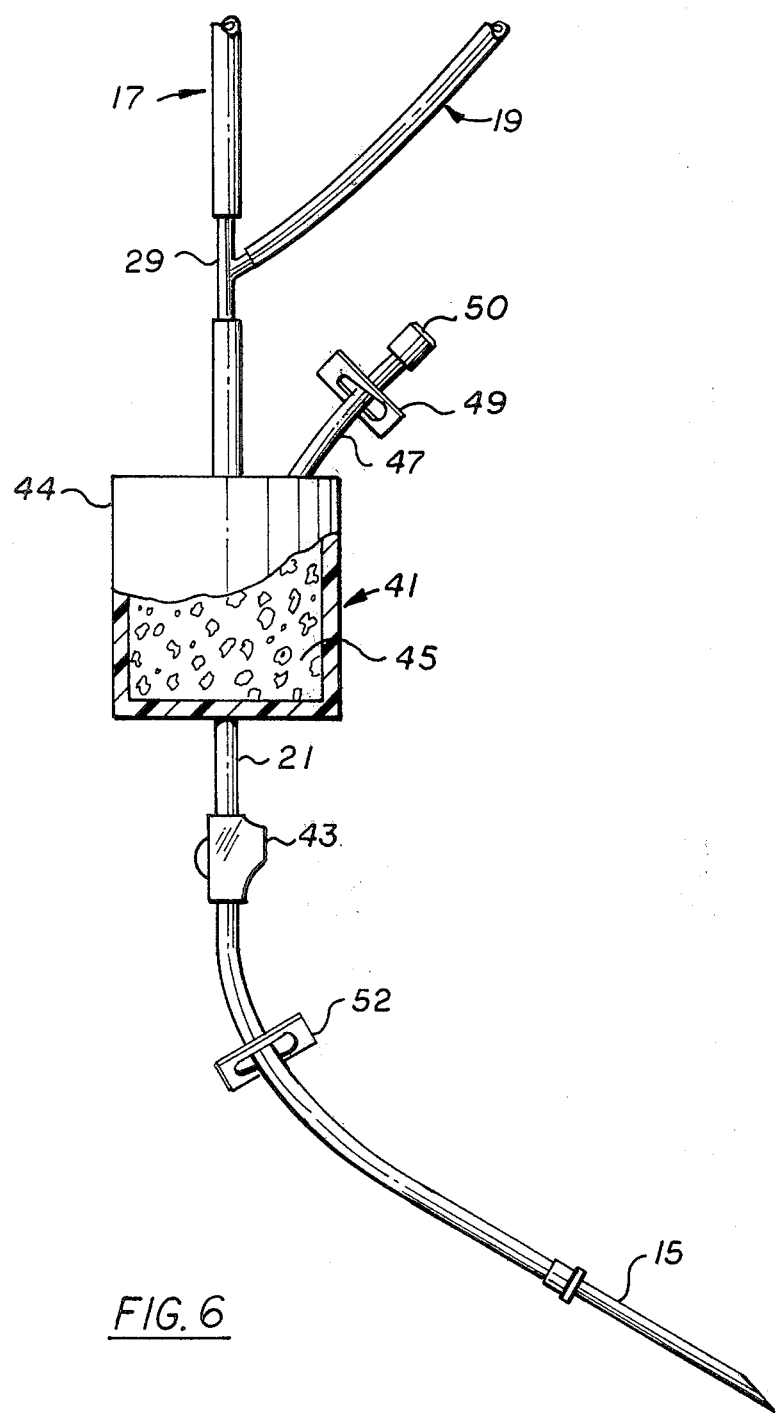
FIG. 6 of the drawings is a front view partially broken away of a medical liquid administration set embodying the system of FIG. 1, with an air filter in the common tube of the set.

The air barrier 41 shown in the sets of FIGS. 4 and 5 comprises a housing 63 that has an inlet and outlet in fluid communication with secondary tube 19 and constitutes a portion of it. The outlet from housing 63 has a float valve 65 which floats away from the outlet when liquid is present in housing 63, but seats or closes over the outlet when no liquid is present. It will be apparent to those skilled in the art that numerous other conventional mechanical valves can be employed to perform the function of float valve 65, so long as the valve forms a barrier impermeable by air when no liquid is present in the housing 63.

In the set of FIG. 4, primary tube 17 includes a priming tube 67 having a slide clamp 69 that controls the flow of primary liquid through priming tube 67. Priming tube 67 is joined in parallel to the main branch of primary tube 17 by y-tubes 71, 72 located on each side of primary control means 31. As will be more fully explained in the following paragraphs, priming tube 17 allows primary control means 31 to remain at its preferred adjustment while the set of FIG. 4 is being primed or backprimed at a higher flow rate.

Primary flow control 31 is shown on the distal side of primary valve 33 in FIGS. 1–5. It has been found that for pressure differentials of the magnitude occuring in the system of this invention, location of primary flow control 31 on the proximal side of primary valve 33, for most of the preferred settings of primary flow control 31, results in a greater pressure being exerted on primary valve 33 by primary liquid than by secondary liquid. As a result, primary valve 33 remains open, as if the height of primary liquid were greater than or equal to the height of secondary liquid in the system.

Surprisingly, it has been found that when primary flow control 31 is located on the distal side of primary valve 33, as shown in FIGS. 1–5, certain embodiments of primary valve 33 might not remain closed as expected whenever the height of primary liquid is less than the height of secondary liquid in the system. This unexpected opening results from the reaction force on primary valve 33 caused by primary liquid that cannot flow upwardly past primary flow control 31 when primary valve 33 initially closes. This reaction force reopens valve 33 and keeps it open.

It has been found that this unexpected opening of primary valve 33 can be obviated by the inclusion in primary tube 17 of a chamber 75 for a compressible mass. As shown in FIG. 5, chamber 75 is located between primary flow control 31 and primary valve 33 and provides a cushion or spring for relieving pressures on the distal side of primary valve 33 whenever valve 33 closes in response to the height of primary liquid being less than the height of secondary liquid in the system. Although primary valve 33 and chamber 75 are shown as separate units in FIG. 5, it will be apparent that they can be combined into one unit, if so desired.

As shown in the set of FIG. 5, chamber 75 has a housing with an inlet and outlet in fluid communication with primary tube 17. However, it is contemplated that chamber 75 can have only one opening in communication with primary tube 17. That is, chamber 75 may have a single opening transverse to the normal flow of liquid through primary tube 17 so that primary liquid only flows in or out of its single opening when reverse flow pressures exist on the distal side of primary valve 33.

Generally, the compressible mass of chamber 75 will be air and its housing will be a rigid opaque plastic. However, it is contemplated that the compressible mass of chamber 75 can be a sponge or other flexible solid materials, as well. Further, the housing of chamber 75 can be a flexible material which is compressible by the primary liquid to expand chamber 75, if so desired.

For simplicity, the equipment sets embodying the system of FIG. 1 have been depicted and described as integral units in FIGS. 2–5. It is apparent, however, that the sets can be manufactured and assembled in subsets of the entire set and that each subset will accordingly be provided such resealable closures, piercing means, adapters etc. as are necessary to permit their easy assemblage into the complete set at an appropriate time. It will also be apparent that each of the several components of the sets of FIGS. 2–5 can be interchanged or combined in combinations other than those specifically depicted.

OPERATION OF THE SYSTEM

As depicted in FIGS. 2–5, primary container 11 is suspended in space at a height above the patient by means of a hook 77 and stand 79. It will be apparent that other means for suspending the containers of this invention are well known.

To insure that all the air that might be forced into the patient has been removed from the set, the set is initially primed by first closing all slide clamps 49, 51, 52 and 69, if present. Piercing pin 23 is then inserted into the resealable closure of primary container 11. Primary flow control 31 and secondary flow control 43 are fully opened. Slide clamp 52 is opened to allow primary liquid to flow through the primary liquid flow path and force all the air therefrom that might be forced into the patient. If chamber 75 is present in primary tube 17, a substantial volume of air will remain therein. Slide clamp 52 is then closed.

Clamp 49 on air vent 47 of air barrier 41 is then opened to allow primary liquid to flow into, or backprime, secondary flow path 19 and force all the air from air barrier 41. Slide clamp 49 is then closed. Alternatively, if the set is fully assembled, slide clamp 51 can be opened to allow primary liquid to force air out of the entire secondary tube 19. Slide clamp 51 is then closed.

During the initial priming of secondary tube 19, it is advantageous to hold secondary tube 19 at a height well below primary container 11. When secondary tube 19 has been primed, it is secured in a convenient place until its subsequent use.

Common tube 21, which preferably has an adapter at its proximal end open to the flow of liquid therefrom, is next connected to needle 15, which will generally have been already inserted into a vein of the patient. Slide clamp 52 will then be opened to allow primary liquid to flow through the primary liquid flow path to the patient's vein. Primary flow control 31 is then adjusted to a setting that will provide the desired flow rate for a prolonged infusion of primary liquid into the patient, generally 10–150 ml./hr. As is well known in the medical practice, that flow rate can be visually observed by viewing and counting drops passing through the primary drip chamber 25.

Subsequently, when it is desired to administer a secondary liquid to a patient, piercing pin 35 of secondary tube 19 is inserted into the resealable closure of secondary container 13. If any portion of secondary tube 19 has not already been primed, it can now be primed with secondary container 13 held at a height well below primary container 11, secondary tube slide clamp 51 opened, common tube slide clamp 52 closed and priming tube slide clamp 69, if present, opened.

Primary liquid then is allowed to flow into, or backprime, secondary tube 19 until all the air that can be forced into the patient has been expelled from secondary tube 19. If present, priming tube 67 allows the primary liquid to bybass the primary flow control and flow into secondary tube 19 at the fastest possible rate.

Secondary container 13 is then suspended in space from stand 79 at a height substantially greater than the height of primary container 11, thereby immediately causing primary valve 33 to close. Priming tube slide clamp 69, if present, is then closed and common tube slide clamp 52 opened. Secondary flow control 43 is then adjusted to a desired flow rate, typically 50-250 ml./hr., for the secondary liquid, which will then flow until the secondary container 13 is depleted. It will be apparent that the initial liquid flowing from secondary tube 19 will be the primary liquid with which it was primed.

The set of FIG. 3 can be employed to administer a specific dose of secondary liquid to the patient by closing secondary tube slide clamp 51 when the desired amount of secondary liquid is in the calibrated cylinder 53. Air vent slide clamp 49 is then opened to allow the secondary liquid to flow from cylinder 53. However, while calibrated cylinder 53 is depicted at a lower height than primary container 11, in FIG. 3, once secondary tube slide clamp 51 is closed, calibrated cylinder 53 must be raised to a height substantially above primary container 11, otherwise concomitant flow of the primary and secondary liquids will occur.

When the height of primary liquid in the system of FIG. 1, as depicted in the sets of FIGS. 2-5, becomes greater than the height of the secondary liquid, primary valve 33 will immediately open and allow primary liquid to flow from the primary container at the flow rate to which primary flow control 31 is adjusted. The primary flow rate is independent of the secondary flow rate. In those instances where it is less than or equal to the secondary flow rate, both primary and secondary liquid will flow through common tube 21, until air reaches air barrier 41 in the secondary tube. Then only primary liquid will enter common tube 21. Air barrier 41 then prevents air from being drawn into common tube 21 and eventually to the patient's vein.

When primary container 11 becomes depleted of primary liquid, the primary piercing pin 23 is merely removed therefrom and inserted into the resealable closure of a new primary container, which is then suspended in place of the previous container. If primary container 11 had become empty, it will be necessary to reprime the entire system as when the first primary container was administered.

When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The secondary tube 19 must then be backprimed, as when the first secondary container was administered.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

We claim:

1. In a set for the sequential administration of medical liquids to a patient, said set including:
   a primary tube for the flow of a primary medical liquid therethrough and including a primary valve for controlling the flow of liquid through said primary tube,
   a secondary tube for the flow of a secondary medical liquid therethrough,
   a common tube having its distal end in fluid communication with the proximal ends of said primary and secondary tube and its proximal end open for the flow of liquid therefrom to form a primary liquid flow path comprising said primary tube and said common tube and a secondary liquid flow path comprising said secondary tube and said common tube, the improvement which comprises:
   a secondary flow control means in said secondary liquid flow path for adjusting the flow rate of said secondary liquid therethrough,
   a primary flow control means on said primary tube for adjusting the flow rate of said primary liquid through said primary flow path to a rate independent of the flow rate of said secondary liquid through said secondary liquid flow path, and
   an air barrier means within said secondary liquid flow path substantially impervious to air but permitting liquid flow there through while said set is in use and preventing the flow of air therethrough after said secondary liquid has been depleted, whereby, following administration of said secondary liquid, flow of said primary liquid may be resumed at the preset rate without adjustment of said primary or said secondary flow control means.

2. The set defined in claim 1, wherein said air barrier comprises a hydrophilic membrane disposed in a housing having an inlet and outlet in fluid communication with said secondary liquid flow path.

3. The set defined in claim 1, wherein said air barrier comprises a mechanical valve disposed in a housing having an inlet and outlet in fluid communication with said secondary liquid flow path.

4. The set defined in claim 3, wherein said mechanical valve is a float valve.

5. The set defined in claim 1, wherein said air barrier is located between the ends of said secondary tube.

6. The set defined in claim 1, wherein said air barrier is located between the ends of said common tube.

7. The set defined in claim 2, wherein said housing includes an air vent.

8. The set defined in claim 7, wherein said air vent is covered by a hydrophobic membrane.

9. The set defined in claim 7, wherein said housing is a calibrated cylinder.

10. The set defined in claim 9, and further including a drip chamber in said secondary tube located on the proximal side of said calibrated cylinder.

11. The set defined in claim 1, wherein said primary tube further includes a primary piercing pin at its distal end for insertion into a container for a primary medical liquid and a drip chamber for forming drops of said primary liquid.

12. The set defined in claim 11, wherein said secondary tube further includes a secondary piercing pin at its distal end for insertion into a container for a secondary medical liquid, and a drip chamber for forming drops of said secondary liquid.

13. The set defined in claim 11 or 12, wherein said piercing pins and drip chambers are integral.

14. The set defined in claim 11 or 12, wherein said piercing pins have integral air vents.

15. The set defined in claim 1, wherein said secondary flow control means is on said secondary tube.

16. The set defined in claim 1, wherein said secondary flow control means is on said common tube.

17. The set defined in claim 1, wherein said primary flow control means is on the distal side of said primary valve and said primary valve is further characterized as a one-way valve that allows said primary liquid to flow towards said common tube, but prevents the flow of said secondary liquid into said primary tube.

18. The set defined in claim 17, wherein said primary tube further includes a priming tube connected thereto in fluid communication on each side of said primary flow control means and having a priming tube flow control means thereon to regulate the flow of said primary liquid through said priming tube.

19. The set defined in claim 17 or 18 and further including a chamber for a compressible mass in fluid communication with said primary tube between said primary flow control means and said primary valve to provide a spring for relieving pressures on said primary valve whenever the height of said primary liquid is less than the height of said secondary liquid in the system.

20. The set defined in claim 19, wherein said chamber has only one opening thereto.

21. The set defined in claim 19, wherein said chamber has an inlet and outlet in communication with said primary tube.

22. The set defined in claim 19, wherein said compressible mass is air.

23. In a set for the sequential administration of medical liquids to a patient, said set including:
a primary tube for the flow of a primary medical liquid therethrough and including a primary valve for controlling the flow of liquid through said primary tube,
a secondary tube for the flow of a secondary medical liquid therethrough,
a common tube having its distal end in fluid communication with the proximal ends of said primary and secondary tube and its proximal end open for the flow of liquid therethrough to form a primary liquid flow path comprising said primary tube and said common tube and a secondary liquid flow path comprising said secondary tube and said common tube, the improvement which comprises:
a secondary flow control means in said secondary liquid flow path for adjusting the flow rate of said secondary liquid therethrough,
a primary flow control means on said primary tube for adjusting the flow rate of said primary liquid through said primary flow path to a rate independent of the flow rate of said secondary liquid through said secondary liquid flow path,
an air barrier in said secondary liquid flow path substantially impervious to air while said set is in use and preventing the flow of air therethrough, and
a chamber for a compressible mass in fluid communication with said primary tube between said primary flow control means and said primary valve to provide a spring for relieving pressures on the distal side of said primary valve whenever the height of said primary liquid is less than the height of said secondary liquid in said system.

24. In a gravitational flow system for the sequential administration of medical liquids to a patient, said system including:
a primary container suspended in space for containing a primary medical liquid,
a primary tube having its distal end in fluid communication with said primary container,
a secondary container suspended in space at a height greater than that of said primary container for containing a secondary medical liquid,
a secondary tube having its distal end in fluid communication with said secondary container,
a common tube having its distal end in fluid communication with the proximal ends of said primary and secondary tubes and its proximal end open for the flow of liquid therefrom to form a primary liquid path comprising said primary tube and said common tube and a secondary liquid flow path comprising said secondary tube and said common tube, and
a primary valve in said primary tube which allows primary liquid to flow from said primary container whenever the height of said primary liquid is greater than or equal to the height of said secondary liquid in said system and which prevents primary liquid from flowing from said primary container whenever the height of said primary liquid is less than the height of said secondary liquid in said system, the improvement which comprises:
an air barrier means within said secondary liquid flow path substantially impervious to air but permitting liquid flow there through while said system is in use and preventing the flow of air therethrough after said secondary liquid has been depleted,
secondary flow control means in said secondary liquid flow path for adjusting the flow rate of said secondary liquid therethrough, and
primary flowing control means on said primary tube for adjusting the flow of said primary liquid through said primary liquid flow path at a rate independent of the flow rate of said secondary liquid through said secondary liquid flow path,
whereby following administration of said secondary liquid, flow of said primary liquid may be resumed at the preset rate without adjustment of said primary or said secondary flow control means.

* * * * *

Notice of Adverse Decision in Interference

In Interference No. 100,817, involving Patent No. 4,256,104, A. J. Muetteries and J. N. Genese, EQUIPMENT SETS AND SYSTEM FOR THE SEQUENTIAL ADMINISTRATION OF MEDICAL LIQUIDS AT DUAL FLOW RATES, final judgment adverse to the patentees was rendered Jan. 8, 1986, as to claims 3, 4 and 6.

[*Official Gazette November 21, 1989*]

UNITED STATES PATENT AND TRADEMARK OFFICE
CERTIFICATE OF CORRECTION

PATENT NO.  : 4,256,104
DATED       : March 17, 1981
INVENTOR(S) : Andrew J. Muetterties, et al.

It is certified that error appears in the above—identified patent and that said Letters Patent is hereby corrected as shown below:

Column 8, Claim 2, line 42, after "claim 1" insert "or 24".
Column 8, Claim 3, line 47, after "claim 1" insert "or 24".
Column 8, Claim 5, line 53, after "claim 1" insert "or 24".
Column 8, Claim 6, line 55, after "claim 1" insert "or 24".
Column 8, Claim 7, line 57, after "claim 2" insert "or 3".
Column 8, Claim 11, line 66, after "claim 1" insert "or 24".
Column 9, Claim 15, line 12, after "claim 1" insert "or 24".
Column 9, Claim 16, line 14, after "claim 1" insert "or 24".
Column 9, Claim 17, line 16, after "claim 1" insert "or 24".
Column 9, Claim 20, line 36, after "claim 19" insert "or 23".
Column 9, Claim 21, line 38, after "claim 19" insert "or 23".
Column 9, Claim 22, line 41, after "claim 19" insert "or 23".

Signed and Sealed this

Twenty-fifth Day of June, 1991

*Attest:*

*Attesting Officer*

HARRY F. MANBECK, JR.

*Commissioner of Patents and Trademarks*